US007249848B2

(12) United States Patent
Laredo et al.

(10) Patent No.: US 7,249,848 B2
(45) Date of Patent: Jul. 31, 2007

(54) WETTABLE HYDROGELS COMPRISING REACTIVE, HYDROPHILIC, POLYMERIC INTERNAL WETTING AGENTS

(75) Inventors: Walter R. Laredo, Hillsborough, NJ (US); Stephen C. Arnold, Flanders, NJ (US); Kevin McCabe, Jacksonville, FL (US); Susan Orr, Jacksonville, FL (US); Azaam Alli, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 10/954,559

(22) Filed: Sep. 30, 2004

(65) Prior Publication Data

US 2006/0072069 A1     Apr. 6, 2006

(51) Int. Cl.
    *G02C 7/04* (2006.01)
(52) U.S. Cl. .............................. 351/160 H; 351/160 R; 424/429
(58) Field of Classification Search ............. 351/160 H
    See application file for complete search history.

(56) References Cited

U.S. PATENT DOCUMENTS

| 3,408,429 A | 10/1968 | Wichterle ................... 264/2.1 |
| 3,660,545 A | 5/1972 | Wichterle ................... 264/2.1 |
| 3,808,178 A | 4/1974 | Gaylord ....................... 526/279 |
| 4,018,853 A | 4/1977 | Le Boeuf et al. ........... 525/283 |
| 4,113,224 A | 9/1978 | Clark et al. ................. 249/105 |
| 4,120,570 A | 10/1978 | Gaylord ....................... 351/247 |
| 4,136,250 A | 1/1979 | Mueller et al. ............... 528/29 |
| 4,153,641 A | 5/1979 | Deichert et al. ............. 526/264 |
| 4,197,266 A | 4/1980 | Clark et al. ................... 264/2.2 |
| 4,495,313 A | 1/1985 | Larsen ......................... 523/106 |
| 4,680,336 A | 7/1987 | Larsen et al. ................ 524/548 |
| 4,740,533 A | 4/1988 | Su et al. ...................... 523/106 |
| 4,889,664 A | 12/1989 | Kindt-Larsen et al. ........ 264/22 |
| 4,910,277 A | 3/1990 | Bambury et al. ............. 526/260 |
| 5,006,622 A | 4/1991 | Kunzler et al. .............. 526/309 |
| 5,034,461 A | 7/1991 | Lai et al. ..................... 525/100 |
| 5,039,459 A | 8/1991 | Kindt-Larsen et al. ....... 264/2.2 |

(Continued)

FOREIGN PATENT DOCUMENTS

EP          0080539 B1          6/1983

(Continued)

OTHER PUBLICATIONS

PCT International Search Report, dated Jan. 19, 2006, for PCT Int'l. Appln. No. PCT/US2005/035149.

(Continued)

*Primary Examiner*—Jordan Schwartz
*Assistant Examiner*—Jessica Stultz
(74) *Attorney, Agent, or Firm*—Karen Harding

(57) ABSTRACT

The present invention relates to wettable silicone hydrogels comprising the reaction product of at least one siloxane containing component and at least one reactive, hydrophilic polymeric internal wetting agent. The present invention further relates to silicone hydrogel contact lenses comprising at least one oxygen permeable component, and an amount of reactive, hydrophilic polymeric internal wetting agent sufficient to impart wettability to said device.

39 Claims, 2 Drawing Sheets

U.S. PATENT DOCUMENTS

| | | | |
|---|---|---|---|
| 5,070,215 A | 12/1991 | Bambury et al. | 556/418 |
| 5,177,165 A | 1/1993 | Valint, Jr. et al. | 526/245 |
| 5,256,751 A | 10/1993 | Vanderlaan | 526/304 |
| 5,311,223 A | 5/1994 | Vanderlaan | 351/160 H |
| 5,321,108 A | 6/1994 | Kunzler et al. | 526/242 |
| 5,352,714 A | 10/1994 | Lai et al. | 523/107 |
| 5,364,918 A | 11/1994 | Valint, Jr. et al. | 526/245 |
| 5,374,662 A | 12/1994 | Lai et al. | 522/172 |
| 5,387,662 A | 2/1995 | Kunzler et al. | 526/245 |
| 5,525,691 A * | 6/1996 | Valint et al. | 526/245 |
| 5,539,016 A | 7/1996 | Kunzler et al. | 528/25 |
| 6,218,503 B1 | 4/2001 | Lai et al. | 528/320 |
| 6,367,929 B1 * | 4/2002 | Maiden et al. | 351/160 H |
| 6,822,016 B2 | 11/2004 | McCabe et al. | 523/107 |
| 2003/0125498 A1 | 7/2003 | McCabe et al. | 528/25 |
| 2005/0176911 A1* | 8/2005 | Zanini et al. | 528/32 |

FOREIGN PATENT DOCUMENTS

| | | |
|---|---|---|
| WO | WO 1996/31792 A1 | 10/1996 |
| WO | WO 03/022321 A2 | 3/2003 |
| WO | WO 03/022322 A2 | 3/2003 |
| WO | WO 2004/081105 | 9/2004 |

OTHER PUBLICATIONS

Crivello J.V. & Dietuker K.; vol. III, Photoinitiators for Free Radical Cationic & Anionic Photopolymerisation, 1998, 275-298, 2nd Edition by edited by G. Bradley; John Wiley and Sons; New York.

ISO 913-1: 1996(E), Optics and Optical Instruments—Contact Lenses—Part 1: Determination of Oxygen Permeability and Transmissibility by the FATT Method, Nov. 1, 1996, 1st Edition, International Organization for Standardization, Geneve, Switzerland.

* cited by examiner

WETTABLE HYDROGELS COMPRISING REACTIVE, HYDROPHILIC, POLYMERIC INTERNAL WETTING AGENTS

FIELD OF THE INVENTION

This invention relates to silicone hydrogels comprising at least one reactive, hydrophilic polymeric internal wetting agent, as well as methods for their production and use.

BACKGROUND OF THE INVENTION

Contact lenses have been used commercially to improve vision since at least the 1950s. The first contact lenses were made of hard materials and as such were somewhat uncomfortable to users. Modern soft contact lenses are made of softer materials, typically hydrogels. Recently soft contact lenses made from silicone hydrogels have been introduced. Silicone hydrogels are water-swollen polymer networks that have high oxygen permeability. However, some users experience discomfort and excessive ocular deposits leading to reduced visual acuity when using these lenses.

Others have tried to alleviate this problem by coating the surface of silicone hydrogel contact lenses with hydrophilic coatings, such as plasma coatings. For example, it has been disclosed that silicone hydrogel lenses can be made more compatible with ocular surfaces by applying plasma coatings to the lens surface or by treating the surface with reactive hydrophilic polymers. Reactive functionalities on or near the surface of medical devices are chemically attached to reactive functional groups on a hydrophilic polymer, thereby creating a hydrophilic surface. In one example, Vinylpyrrolidone-co-4-vinylcyclohexyl-1,2-epoxide polymer was used to coat a silicone substrate. However, surface modifications are usually added steps in contact lens production.

Surface active macromonomers comprising 10-90% repeating units from ethylenically unsaturated hydrophobic monomer have been disclosed for use in contact lens applications. A 2-step reaction is carried out to form a PVP-methacrylate. The total process involves several synthetic steps and, as a result, requires extensive purification of each intermediate. The resultant "surface-active macromonomers" are low in molecular weight with Mn, Mw, and polydispersity values of 4,900, 8,900, and 1.8, respectively (versus PEG standards). The inclusion of substantial quantities of hydrophobic monomers may prevent the formation of wettable contact lenses. Wettability data for lens wear longer than one hour is not reported.

Incorporation of internal hydrophilic wetting agents into a macromer containing reaction mixture has been disclosed. However, not all silicone containing macromers display compatibility with hydrophilic polymers. Modifying the surface of a polymeric article by adding polymerizable surfactants to a monomer mix used to form the article has also been disclosed. However, lasting in vivo improvements in wettability and reductions in surface deposits are not likely.

Poly(N-vinyl-2-pyrrolidone) (PVP) or poly-2-ethyl-2-oxazoline have been added to hydrogel compositions to form interpenetrating networks which show a low degree of surface friction, a low dehydration rate and a high degree of biodeposit resistance.

It has been previously shown that high molecular weight (Mw>300,000) PVP can be entrapped within a cross-linked silicone hydrogel matrix. However, a small loss of the high molecular weight PVP (<10 weight percent) is still observed during the extraction purification process in organic solvents.

Therefore it would be advantageous to find additional hydrophilic polymers which may be incorporated into a lens formulation to improve wettability of the lens without a surface treatment.

SUMMARY OF THE INVENTION

The present invention relates to reactive, hydrophilic polymeric internal wetting agents for use in biomedical devices.

The present invention further relates to a wettable silicone hydrogel comprising the reaction product of at least one siloxane containing component and at least one reactive, hydrophilic polymeric internal wetting agent.

The present invention further relates to silicone hydrogel contact lenses comprising at least one oxygen permeable component, and an amount of reactive, hydrophilic polymeric internal wetting agent sufficient to impart wettability to said device.

DETAILED DESCRIPTION OF THE INVENTION

Figure 1:
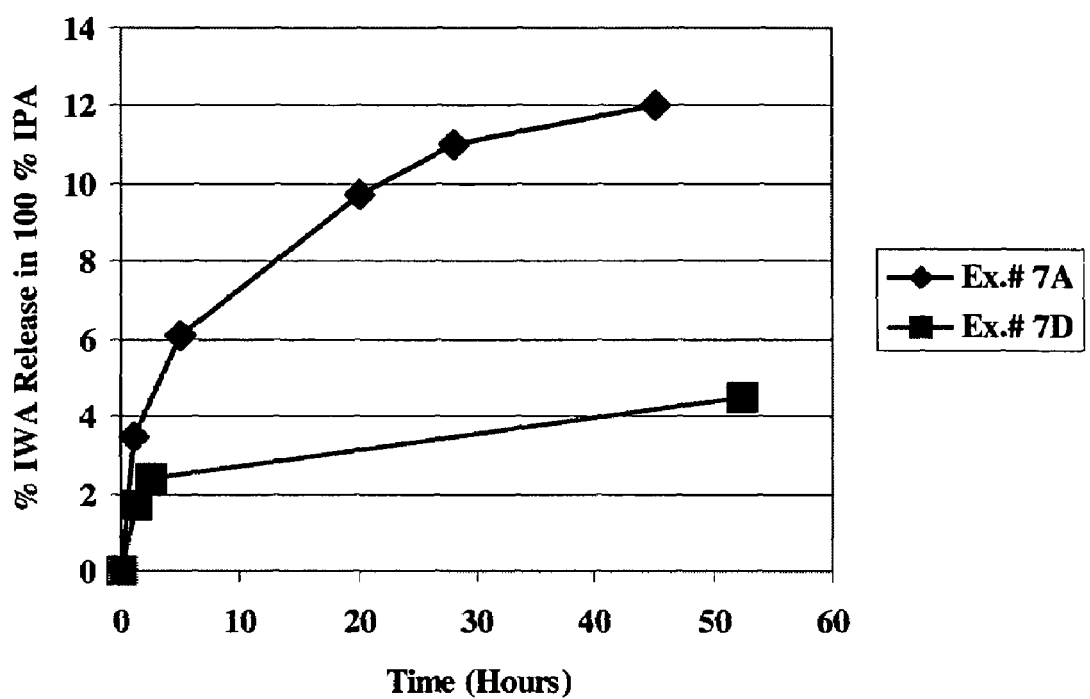
FIG. 1 is a graph showing percent loss of reactive and non-reactive hydrophilic polymeric internal wetting agents.
Figure 2:
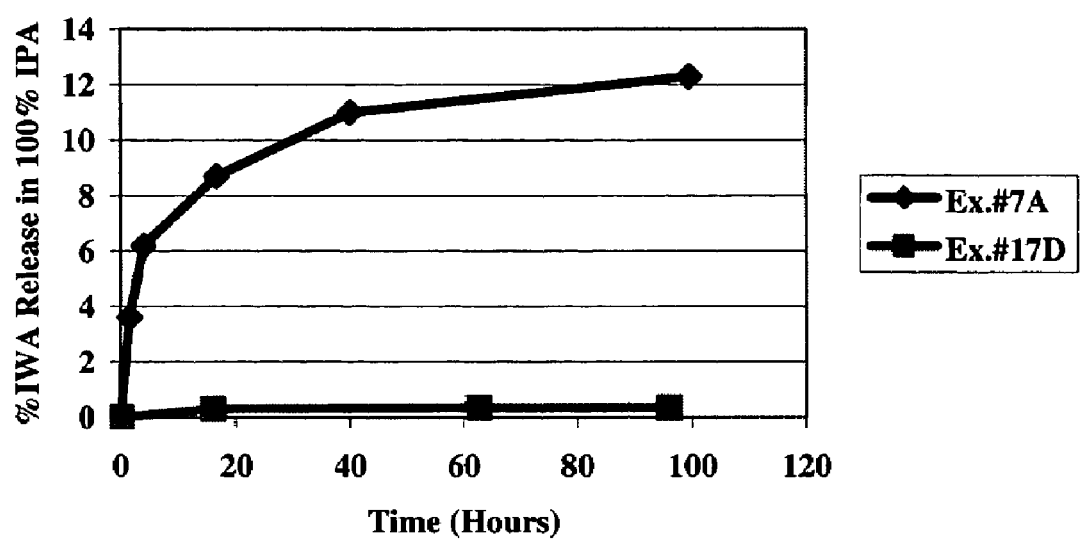
FIG. 2 is a graph showing percent loss of reactive and non-reactive hydrophilic polymeric internal wetting agents.

As used herein, a "biomedical device" is any article that is designed to be used while either in or on mammalian tissues or fluid, and preferably in or on human tissue or fluids. Examples of these devices include but are not limited to catheters, implants, stents, and ophthalmic devices such as intraocular lenses and contact lenses. The preferred biomedical devices are ophthalmic devices, particularly contact lenses, most particularly contact lenses made from silicone hydrogels.

As used herein, the terms "lens" and "ophthalmic device" refer to devices that reside in or on the eye. These devices can provide optical correction, wound care, drug delivery, diagnostic functionality, cosmetic enhancement or effect or a combination of these properties. The term lens includes but is not limited to soft contact lenses, hard contact lenses, intraocular lenses, overlay lenses, ocular inserts, and optical inserts.

As used herein, the phrase "without a surface treatment" means that the exterior surfaces of the devices of the present invention are not separately treated to improve the wettability of the device. Treatments which may be foregone because of the present invention include, plasma treatments, grafting, coating and the like. However, coatings which provide properties other than improved wettability, such as, but not limited to antimicrobial coatings and the application of color or other cosmetic enhancement may be applied to devices of the present invention.

As used herein the term "silicone containing compatibilizing component" means reaction components which contain at least one silicone and at least one hydroxyl group. Such components have been disclosed in U.S. Ser. Nos. 10/236,538 and 10/236,762.

As used herein, "macromer" is a low molecular weight polymer having at least one polymerizable end group and a degree of polymerization (DP) ranging from 10 to 1000 monomeric repeat units, which correspond to a number average molecular weight range from approximately 100 to approximately 100,000 Daltons.

As used herein the term "monomer" is a compound containing at least one polymerizable group and an average molecular weight of about less than 2000 Daltons, as measured via gel permeation chromatography using refractive index detection.

The compositions of the present invention comprise, consist essentially and consist of at least one silicone containing component and at least one reactive, hydrophilic polymeric internal wetting agent. As used herein, "reactive, hydrophilic polymeric internal wetting agent" refers to substances having a weight average molecular weight of at least about 2000 Daltons, wherein said substances upon incorporation to silicone hydrogel formulations, improve the wettability of the cured silicone hydrogels. The reactive, hydrophilic polymeric internal wetting agents may have a wide range of molecular weights (weight average). Molecular weights of greater than about 5,000 Daltons; more preferably between about 5,000 to about 2,000,000 Daltons are suitable. In some embodiments lower molecular weights from between about 5,000 to about 180,000 Daltons, most preferably about 5,000 to about 150,000 Daltons may be preferred, while in others higher molecular weight ranges, from about 60,000 to about 2,000,000 Daltons, preferably between about 100,000 to about 1,800,000 Daltons, more preferably about 180,000 to about 1,500,000 Daltons and most preferably from about 180,000 to about 1,000,000 (all weight average molecular weight) may be used.

The molecular weights for polymers having a molecular weight greater than about 2000 Daltons may be determined by gel permeation chromatography (GPC) {size exclusion chromatography (SEC)} using hexafluoroisopropanol as solvent, and relate, unless otherwise stated, to poly(2-vinylpyridine) calibration standards.

The reactive, hydrophilic polymeric internal wetting agents ("IWAs") of the present invention comprise at least 90% and preferably at least about 95% repeating units from hydrophilic components. As used herein a hydrophilic component is one which when polymerized with a small amount of crosslinking monomer, forms a polymer capable of absorbing at least about 5 wt % water, preferably more than about 10 wt % water, and in some cases more than about 20% water.

As used herein, "reactive" means any group that can undergo anionic, cationic or free radical polymerization. Free radical reactive groups include acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, $C_{2-12}$alkenylphenyls, $C_{2-12}$alkenylnaphthyls, or $C_{2-6}$alkenylphenyl$C_{1-6}$alkyls. Cationic reactive groups include vinyl ethers, epoxide groups and mixtures thereof. Preferred reactive groups include methacrylates, acryloxys, methacrylamides, acrylamides, and mixtures thereof. The reactive, hydrophilic polymeric IWAs of the present invention may have one or more reactive group. In one embodiment the reactive, hydrophilic, polymeric IWAs have one reactive group on a terminal end.

The reactive, hydrophilic polymeric internal wetting agents are present in the formulations of these devices in an amount sufficient to provide contact lenses, which without surface modification remain substantially free from surface depositions during use. Typical use periods include at least about 8 hours, and preferably worn several days in a row, and more preferably for 24 hours or more without removal. Substantially free from surface deposition means that, when viewed with a slit lamp, at least about 80 percent and preferably at least about 90 percent, and more preferably about 100 percent of the lenses worn in the patient population display depositions rated as none or slight, over the wear period.

Suitable amounts of reactive, hydrophilic polymeric internal wetting agent include from about 1 to about 15 weight percent, more preferably about 3 to about 15 percent, most preferably about 5 to about 12 percent, all based upon the total weight of all reactive components.

Examples of reactive, hydrophilic polymeric internal wetting agents include but are not limited to reactive, hydrophilic polymers derived from polyamides, polylactones, polyimides, polylactams and functionalized polyamides, polylactones, polyimides, polylactams, such as N,N-dimethyl acrylamide (DMA) functionalized by initiating the polymerization of DMA with a lesser molar amount of a hydroxyl-functionalized azo initiator (such as, for example, 2,2'-Azobis{2-[1-(2-hydroxyethyl)-2-imidazolin-2-yl]propane}dihydrochloride, 2,2'-Azobis{2-methyl-N-[1,1-bis(hydroxymethyl)-2-hydroxyethyl]propionamide, 2,2'-Azobis[2-methyl-N-(2-hydroxyethyl)propionamide], or 2,2'-Azobis {2-methyl-N-[2-(1-hydroxybutyl)]propionamide}) and then reacting the hydroxyl groups of the resulting hydrophilic polymer with materials containing radical polymerizable compounds, such as, but not limited to 2-isocyanatoethyl methacrylate, methacrylic anhydride, 3-isopropenyl-alpha, alpha-dimethylbenzyl isocyanate or methacryloyl chloride to form the reactive, hydrophilic polymeric IWA. In one embodiment, the reactive, hydrophilic polymeric internal wetting agents comprise N groups either in the polymer backbone, in pendant groups, or both. The reactive hydrophilic polymeric IWA may comprise DMA, oxazolines or N-vinyl pyrrolidone and can be treated with glycidyl methacrylate as an end-capping reagent. The glycidyl methacrylate groups can be ring-opened to give hydroxyl groups that may be used in conjunction with another hydrophilic prepolymer in a mixed system to increase the compatibility of the reactive, hydrophilic polymeric IWA, and any other groups that impart compatibility. Examples of the above compounds include hydrophilic polymers of Formulae I and reactive, hydrophilic polymeric internal wetting agents of Formulae II

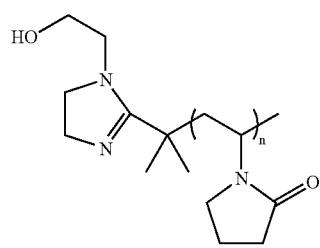

I

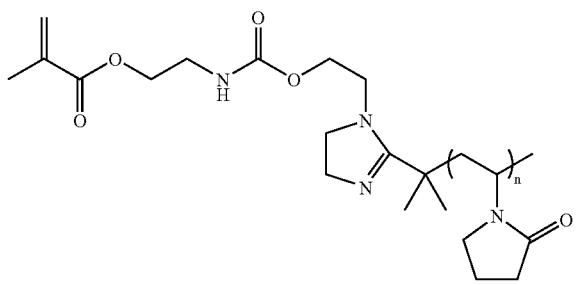

n = 25–500

In another example, reactive, hydrophilic polymeric IWAs can be made by initiating the polymerization of a monomer (such as, for example, DMA) with a lesser molar amount of an amine-functionalized azo initiator (such as, for example, 2,2'-Azobis(2-methylpropionamide)dihydrochloride) and then reacting the amine groups of the resulting low molecular weight polymers with materials containing free radical polymerizable groups, such as 2-isocyanatoethyl methacrylate, 3-isopropenyl-alpha, alpha-dimethylbenzyl isocyanate, methacrylic anhydride, acrylic acid, methacrylic acid, acryloyl chloride, or methacryloyl chloride. Examples of the above compounds include low molecular weight hydrophilic polymers of Formulae III and reactive, hydrophilic polymeric IWAs of Formulae IV.

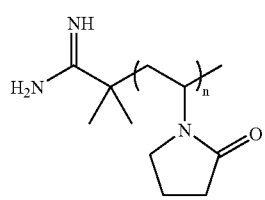

III

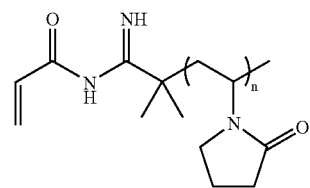

IV n = 25–500

In yet a further example, reactive, hydrophilic polymeric IWAs can also be made by initiating the polymerization of a monomer (such as, for example, DMA) with a lesser molar amount of a carboxylic acid-functionalized azo initiator (such as, for example, 2,2'-Azobis[N-(2-carboxyethyl)-2-methylpropionamidine]tetrahydrate) and then reacting the carboxylic acid groups of the resulting low molecular weight hydrophilic polymer with materials containing free radical polymerizable groups, such as, for example, 2-aminoethyl methacrylate or 3-aminopropyl methacrylamide.

A person skilled in the art will recognize that incomplete reaction between the low molecular weight hydrophilic polymer and the free radical polymerizable compound results in a mixture of products which include, in part, the starting low molecular weight hydrophilic polymer, the reactive hydrophilic polymeric IWA, and unreacted free radical polymerizable compounds. If low molecular weight hydrophilic polymer is present in the final product mixture, it is not essential to remove it from the product mixture. Instead, the low molecular weight hydrophilic polymer may remain, serve as a diluent in the contact lens formulation and be removed later during the purification of the lenses. Those of skill in the art will also recognize that molecular weights of the reactive, hydrophilic polymeric IWAs will vary depending on the reaction parameters, such as amount of initiator present, reaction temperature, and monomer concentration. In addition, the presence of chain transfer agents such thioglycolic acid and thiolactic acid can also be used to control the molecular weights of the reactive, hydrophilic polymeric IWAs.

Examples of the above compounds include low molecular weight hydrophilic polymers of Formulae V and reactive, hydrophilic polymeric internal wetting agents of Formulae VI and VII.

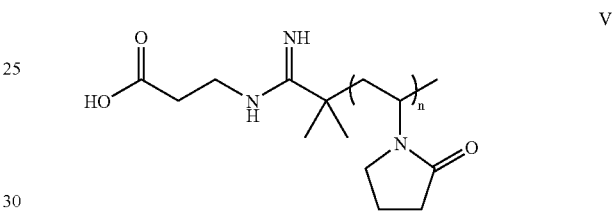

V

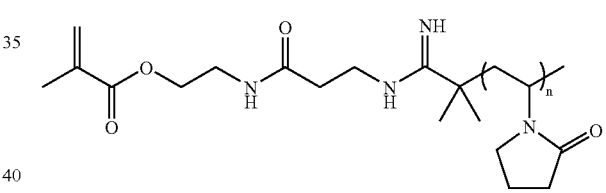

VI

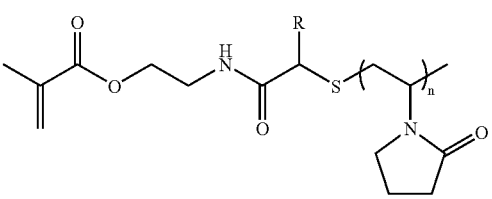

VII n = 25–500
R = H, CH$_3$

One preferred class of reactive, hydrophilic polymeric IWAs include those that contain a cyclic moiety in their backbone, more preferably, a cyclic amide or cyclic imide. Reactive, hydrophilic polymeric IWAs include but are not limited to macromers derived from poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N-N-dimethylacrylamide, polyvinyl alcohol, polyacrylic acid, polyethylene oxide, poly-2-(ethyl-oxazoline), heparin polysaccharides, polysaccharides, mixtures and copolymers (including block or random, branched, multichain, comb-shaped or star shaped) thereof where poly-N-vinylpyrrolidone (PVP) is particularly preferred. Copolymers might also be used such as graft copolymers of PVP. These lactam containing polymers may also be made reactive by treatment with alkali and transition metal borohydrides, such as sodium borohydride (NaBH$_4$), zinc borohydride, sodium triacetoxyborohydride, bis(isopropoxytitanium) borohydride in solution, followed by reaction with suitable polymerizable groups.

Another class of preferred reactive, hydrophilic polymeric IWAs include reactive polymers and copolymers comprising pendant acyclic amide groups capable of association with hydroxyl groups.

Examples of suitable reactive, hydrophilic polymeric IWAs include polymers and copolymers comprising, in the backbone, repeating units of Formula VIII

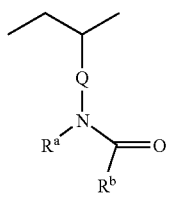

Wherein Q is a direct bond,

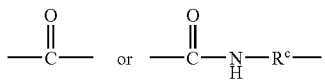

wherein $R^c$ is a C1 to C3 alkyl group;

$R^a$ is selected from H, straight or branched, substituted or unsubstituted C1 to C4 alkyl groups, $R^b$ is selected from H, straight or branched, substituted or unsubstituted C1 to C4 alkyl groups, amino groups having up to two carbons, amide groups having up to 4 carbon atoms and alkoxy groups having up to two carbons and wherein the number of carbon atoms in $R^a$ and $R^b$ taken together is 8, preferably 6 or less. As used herein substituted alkyl groups include alkyl groups substituted with an amine, amide, ether or carboxy group.

In one preferred embodiment $R^a$ and $R^b$ are independently selected from H, and substituted or unsubstituted C1 to C2 alkyl groups and preferably unsubstituted C1 to C2 alkyl groups.

In another preferred embodiment Q is a direct bond, $R^a$ and $R^b$ are independently selected from H, substituted or unsubstituted C1 to C2 alkyl groups.

Preferably the reactive, hydrophilic polymeric IWAs of the present invention comprise a majority of the repeating unit of Formula VIII, and more preferably at least about 80 mole % of the repeating unit of Formula VIII.

Specific examples of repeating units of Formula VIII include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N,N'-dimethylurea, and the following acyclic polyamides:

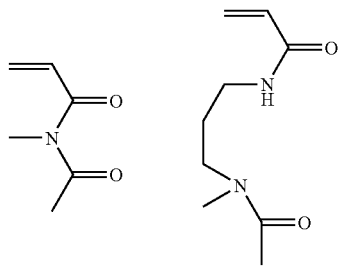

Additional repeating units may be formed from monomers selected from N-vinyl amides, acrylamides, hydroxyalkyl (meth) acrylates, alkyl (meth)acrylates or other hydrophilic monomers and siloxane substituted acrylates or methacrylates. Specific examples of monomers which may be used to form reactive, hydrophilic polymeric IWAs include as N-vinylpyrrolidone, N,N-dimethylacrylamide, 2-hydroxyethylmethacrylate, vinyl acetate, acrylonitrile, methyl methacrylate, hydroxypropyl methacrylate, 2-hydroxyethyl acrylate, and butyl methacrylate, methacryloxypropyl tristrimethylsiloxysilane and the like and mixtures thereof. Preferred additional repeating units monomers include of N-vinylpyrrolidone, N,N-dimethylacrylamide, 2-hydroxyethylmethacrylate and mixtures thereof.

In one embodiment the reactive, hydrophilic polymeric IWA comprises poly(N-vinyl-N-methylacetamide).

In yet another embodiment the reactive, hydrophilic polymeric IWA comprises a reactive high molecular weight copolymer derived from monomers comprising vinyllactam monomers and vinyl carboxylate monomers. Preferably the reactive high molecular weight copolymers have molecular weights (weight average) of at least about 60,000 Daltons, more preferably between about 60,000 to about 750,000 Daltons, more preferably still between about 100,000 to about 600,000 Daltons, and most preferably between about 180,000 to about 500,000 Daltons.

In one embodiment these reactive high molecular weight copolymers may be synthesized in 3 steps. In the first step, a vinyllactam monomer and a vinyl carboxylate monomer are copolymerized using a free radical initiator, resulting in a high molecular weight hydrophilic copolymer. In the second step, the carboxylate groups of the resultant copolymer are partially or completely hydrolyzed under appropriate reaction conditions, resulting in a "modified" high molecular weight copolymer that is capable of further reacting with one or more photo-polymerizable compounds via hydroxyl groups on the polymer backbone. Partial hydrolysis gives terpolymers comprising the units vinyllactam, vinyl alcohol, and vinyl carboxylate, for example a terpolymer of vinylpyrrolidone, vinyl acetate, and vinyl alcohol. In the third step, the modified high molecular weight hydrophilic copolymer is treated with a reactive group, as defined above, to generate the reactive, hydrophilic polymeric IWA.

Suitable N-vinyllactams include N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2- pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl4,6-dimethyl-2-caprolactam, N-vinyl-3,5,7-trimethyl-2-caprolactam, N-vinylmaleimide, vinylsuccinimide, mixtures thereof and the like.

Preferred vinyllactams include heterocyclic monomers containing 4 carbon atoms in the heterocyclic ring. A highly preferred vinyllactam is N-vinyl-2-pyrrolidone.

Suitable vinyl carboxylate include compounds having both vinyl and carboxylate functionality, preferably having up to 10 carbon atoms. Specific examples of suitable vinyl carboxylates include vinyl heptanoate, vinyl hexanoate, vinyl pentanoate, vinyl butanoate, vinyl propanoate (vinyl propionate), vinyl ethanoate (vinyl acetate), vinyl trifluoroacetate, mixtures thereof and the like. A preferred vinyl carboxylate is vinyl acetate.

The high molecular weight copolymers may further comprise repeat units derived from vinyl alcohols. Suitable vinyl alcohols include 2-hydroxyethyl 2-methyl-2-propenoate, p-hydroxystyrene, 4-vinylbenzyl alcohol, diethylene glycol monomethacrylate, 2-[2-(2-hydroxyethoxy)ethoxy]ethyl 2-methyl-2-propenoate, 2,3-Dihydroxypropyl methacrylate, 2-hydroxy-1-(hydroxymethyl)ethyl 2-methyl-2-propenoate, 2-hydroxyethyl acrylate, 2-hydroxypropyl acrylate, butanediol monoacrylate, butanediol monomethacrylate, 3-[(4-ethenylphenyl)methoxy]-1,2-propanediol, 3-(ethenylphenyl)methoxy-1,2-propanediol mix of m-and p-isomers, 2-(ethenylphenyl)methoxyacetic acid mixture of m- and p-isomers, xylitol 1-methacrylate and xylitol 3-methacrylate, N-2-hydroxyethyl methacrylamide, N-2-hydroxyethyl acrylamide.

A class of reactive, hydrophilic polymeric IWAs of this embodiment comprise units in their polymer chain derived from the following monomer units (all numbers are preceded by the word "about"):

| Vinyllactam | Concentration (mole %) | | Reactive group |
|---|---|---|---|
| | vinyl alcohol | vinyl carboxylate | |
| 85–99.9 | 0.1–15 | 0–15 | 0.1–15 |
| 85–99 | 0.1–10 | 0–10 | 0.1–10 |
| 85–99 | 0.1–10 | 0–5 | 0.1–5 |

The reactive, hydrophilic polymeric IWAs formed from high molecular weight copolymers may also be formed from copolymers derived from polyamides, polylactones, polyimides, polylactams and functionalized polyamides, polylactones, polyimides, polylactams, polycarboxylates, such as N-vinyl-2-pyrrolidone (NVP) and vinyl acetate (VA) functionalized by initiating the polymerization of NVP and VA with a lesser molar amount of an azo initiator, hydrolyzing or partially hydrolyzing the carboxylate groups, and then reacting the hydroxyl groups of the resulting high molecular weight hydrophilic copolymer with materials containing radical polymerizable groups, such as 2-isocyanatoethyl methacrylate, methacrylic anhydride, acryloyl chloride, or methacryloyl chloride to form the high molecular weight photo-polymerizable hydrophilic copolymer (HMWPPHC). Suitable azo catalysts are known in the art and include AIBN, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl] propionamide, 2,2'-azobis[2-methyl-N-(2-hydroxyethyl) propionamide], 2,2'-azobis{2-methyl-N-[2-(1-hydroxybutyl)]propionamide}, 2,2'-azobis(2-methylpropionamide)dihydrochloride, or 2,2'-azobis[N-(2-carboxyethyl)-2-methylpropionamidine]tetrahydrate).

Reactive, hydrophilic polymeric IWAs made with glycidyl methacrylate may also be used. The glycidyl methacrylate ring can be opened to give a diol that may be used in conjunction with another hydrophilic polymer in a mixed system to increase the compatibility of the reactive, hydrophilic polymeric IWAs, compatibilizing components and any other groups that impart compatibility. Examples of the above described reactive, hydrophilic polymeric IWAs include compounds Formulae IX and X

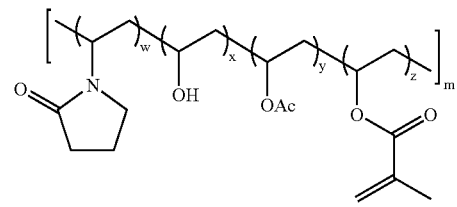

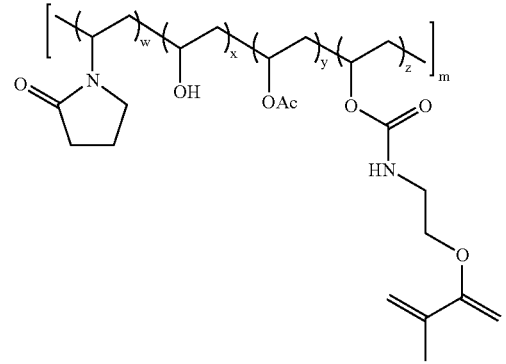

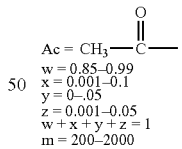

w = 0.85–0.99
x = 0.001–0.1
y = 0–.05
z = 0.001–0.05
w + x + y + z = 1
m = 200–2000

The reactive, hydrophilic polymeric IWAs may be used in amounts from about 1 to about 15 weight percent, more preferably about 3 to about 15 percent, most preferably about 5 to about 12 percent, all based upon the total of all reactive components.

In some embodiments it is preferred that the reactive, hydrophilic polymeric IWA be soluble in the diluent at processing temperatures. Manufacturing processes that use water or water-soluble diluents may be preferred due to their simplicity and reduced cost. In these embodiments reactive, hydrophilic polymeric IWAs that are water soluble at processing temperatures are preferred.

In addition to the reactive, hydrophilic polymeric IWAs, the hydrogels of the present invention further comprise one or more silicone-containing components and, optionally one or more hydrophilic components. The silicone-containing and hydrophilic components used to make the polymer of this invention can be any of the known components used in the prior art to make silicone hydrogels. These terms silicone-containing component and hydrophilic component are not mutually exclusive, in that, the silicone-containing component can be somewhat hydrophilic and the hydrophilic component can comprise some silicone, because the silicone-containing component can have hydrophilic groups and the hydrophilic components can have silicone groups.

Further, silicone-containing component(s) and hydrophilic component(s) can be reacted prior to polymerization to form a prepolymer which is later polymerized in the presence of a diluent to form the polymer of this invention. When prepolymers or macromers are used, it is preferred to polymerize at least one silicone-containing monomer and at least one hydrophilic monomer in the presence of the diluent, wherein the silicone-containing monomers and the hydrophilic monomers differ. The term "monomer" used herein refers to low molecular weight compounds (i.e. typically having number average molecular weights less than 700) that can be polymerized. Thus, it is understood that the terms "silicone-containing components" and "hydrophilic components" include monomers, macromonomers and prepolymers.

A silicone-containing component is one that contains at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone-containing components which are useful in this invention may be found in U.S. Pat. Nos. 3,808,178; 4,120,570; 4,136,250; 4,153,641; 4,740,533; 5,034,461 and 5,070,215, and EP080539. All of the patents cited herein are hereby incorporated in their entireties by reference. These references disclose many examples of olefinic silicone-containing components.

Further examples of suitable silicone-containing monomers are polysiloxanylalkyl(meth)acrylic monomers represented by the following formula:

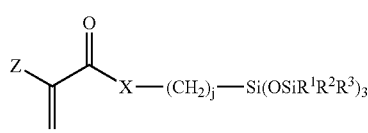

Formula XI wherein: Z denotes H or lower alkyl and preferably H or methyl; X denotes O or $NR^4$; each $R^4$ independently denotes hydrogen or methyl, each $R^1$-$R^3$ independently denotes a lower alkyl radical or a phenyl radical, and j is 1 or 3 to 10.

Examples of these polysiloxanylalkyl (meth)acrylic monomers include methacryloxypropyl tris(trimethylsiloxy)silane, pentamethyldisiloxanyl methylmethacrylate, and methyldi(trimethylsiloxy)methacryloxymethyl silane. Methacryloxypropyl tris(trimethylsiloxy)silane is the most preferred.

One preferred class of silicone-containing components is a poly(organosiloxane) prepolymer represented by Formula XII:

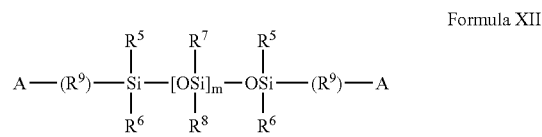

Formula XII wherein each A independently denotes an activated unsaturated group, such as an ester or amide of an acrylic or a methacrylic acid or an alkyl or aryl group (providing that at least one A comprises an activated unsaturated group capable of undergoing radical polymerization); each of $R^5$, $R^6$, $R^7$ and $R^8$ are independently selected from the group consisting of a monovalent hydrocarbon radical or a halogen substituted monovalent hydrocarbon radical having 1 to 18 carbon atoms which may have ether linkages between carbon atoms;

$R^9$ denotes a divalent hydrocarbon radical having from 1 to 22 carbon atoms, and m is 0 or an integer greater than or equal to 1, and preferable 5 to 400, and more preferably 10 to 300. One specific example is α, ω-bismethacryloxypropyl poly-dimethylsiloxane. Another preferred example is mPDMS (monomethacryloxypropyl terminated mono-n-butyl terminated polydimethylsiloxane).

Another useful class of silicone containing components includes silicone-containing vinyl carbonate or vinyl carbamate monomers of the following formula:

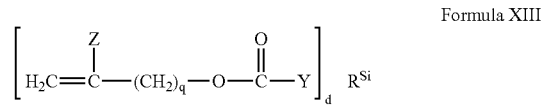

Formula XIII wherein: Y denotes O, S or NH; $R^{Si}$ denotes a silicone-containing organic radical; R denotes hydrogen or lower alkyl, and preferably H or methyl; d is 1, 2, 3 or 4; and q is 0 or 1. Suitable silicone-containing organic radicals $R^{Si}$ include the following:

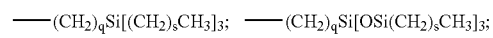

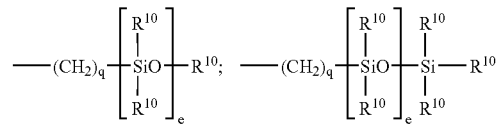

wherein:

$R^{10}$ denotes

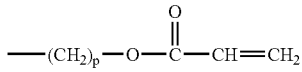

Wherein p is 1 to 6; or an alkyl radical or a fluoroalkyl radical having 1 to 6 carbon atoms; e is 1 to 200; q is 1, 2, 3 or 4; and s is 0, 1, 2, 3, 4 or 5.

The silicone-containing vinyl carbonate or vinyl carbamate monomers specifically include: 1,3-bis[4-(vinyloxycarbonyloxy)but-1-yl]tetramethyl-isiloxane 3-(vinyloxycarbonylthio) propyl-[tris (trimethylsiloxysilane]; 3-[tris(trimethylsiloxy)silyl] propyl allyl carbamate; 3-[tris(trimethylsiloxy)wilyl] propyl vinyl carbamate; trimethylsilylethyl vinyl carbonate; trimethylsilylmethyl vinyl carbonate, and

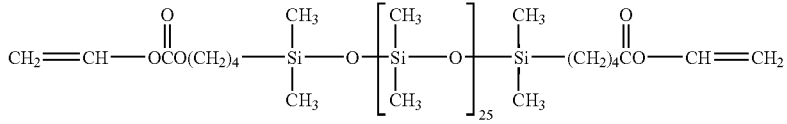

Another class of silicone-containing components includes compounds of the following formulae:

$(*D*A*D*G)_a *D*D*E^1;$ $E(*D*G*D*A)_a *D*G*D*E^1$ or;

$E(*D*A*D*G)_a *D*A*D*E^1$    Formulae XIV-XV wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$_a$ is at least 1;

A denotes a divalent polymeric radical of formula:

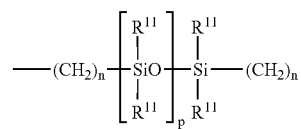

Formula XVI $R^{11}$ independently denotes an alkyl or fluoro-substituted alkyl group having 1 to 10 carbon atoms which may contain ether linkages between carbon atoms; r is at least 1; and p provides a moiety weight of 400 to 10,000; each of E and $E^1$ independently denotes a polymerizable unsaturated organic radical represented by formula:

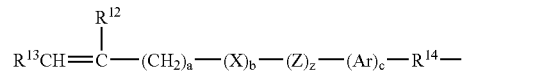

Formula XVII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; a is 0 to 6; b is 0 or 1; e is 0 or 1; and c is 0 or 1.

A preferred silicone-containing component is represented by the following formula:

Formula XVIII

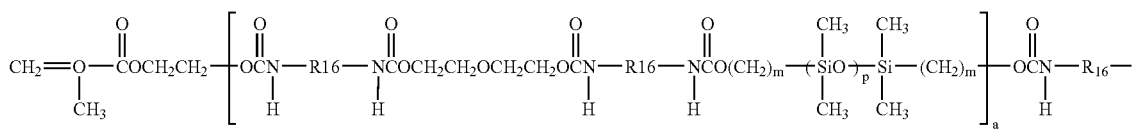

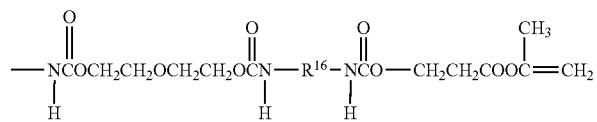

wherein $R^{16}$ is a diradical of a diisocyanate after removal of the isocyanate group, such as the diradical of isophorone diisocyanate. Another preferred silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula XIX

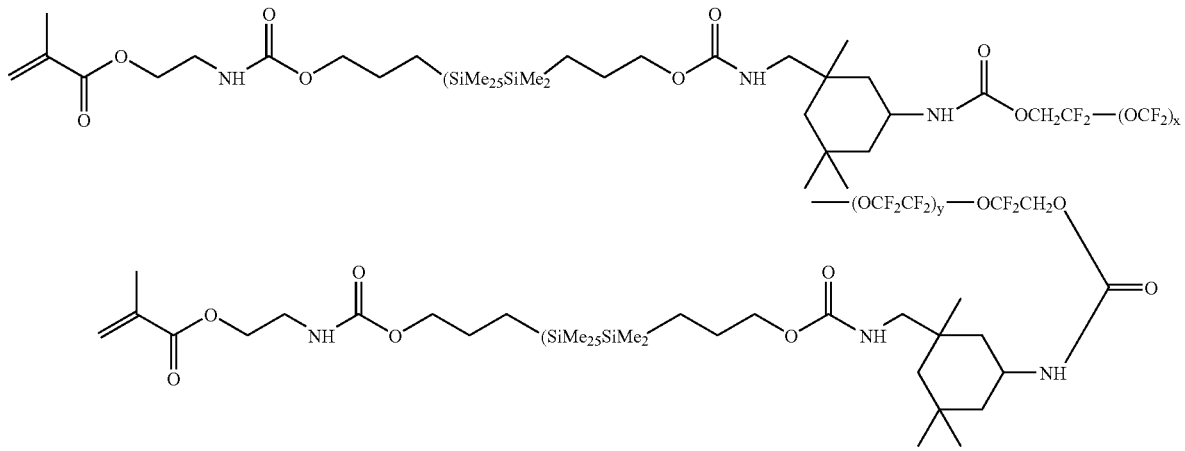

Other silicone-containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662 and 5,539,016 describe polysiloxanes with a polar fluorinated graft or side group having a hydrogen atom attached to a terminal difluoro-substituted carbon atom. Such polysiloxanes can also be used as the silicone monomer in this invention.

The hydrogels may further comprise hydrophilic components, such as those which are capable of providing at least about 20% and preferably at least about 25% water content to the resulting lens when combined with the remaining reactive components. When present, suitable hydrophilic components may be present in amounts up to about 60 weight %, preferably between about 10 to about 60 weight %, more preferably between about 15 to about 50 weight % and more preferably still between about 20 to about 40 weight %, all based upon the weight of all reactive components. The hydrophilic monomers that may be used to make the polymers of this invention have at least one polymerizable double bond and at least one hydrophilic functional group. Examples of functional groups with polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. Such hydrophilic monomers may themselves be used as crosslinking agents. "Acrylic-type" or "acrylic-containing" monomers are those monomers containing the acrylic group

(CR'H=CRCOX)

wherein R is H or $CH_3$, R' is H, alkyl or carbonyl, and X is O or N, which are also known to polymerize readily, such as N,N-dimethylacrylamide (DMA), 2-hydroxyethyl acrylate, glycerol methacrylate, 2-hydroxyethyl methacrylamide, polyethyleneglycol monomethacrylate, methacrylic acid, acrylic acid and mixtures thereof.

Hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, N-2-hydroxyethyl vinyl carbamate, N-carboxy-β-alanine N-vinyl ester, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol with one or more of the terminal hydroxyl groups replaced with a functional group containing a polymerizable double bond. Examples include polyethylene glycol reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

More preferred hydrophilic monomers which may be incorporated into the polymer of the present invention include hydrophilic monomers such as N,N-dimethyl acrylamide (DMA), 2-hydroxyethyl acrylate, glycerol methacrylate, 2-hydroxyethyl methacrylamide, N-vinylpyrrolidone (NVP), and polyethyleneglycol monomethacrylate.

Most preferred hydrophilic monomers include DMA, NVP and mixtures thereof.

When the reactive, hydrophilic polymeric IWAs of the present invention are incorporated into a silicone hydrogel formulation, it may be desirable to include at least one a hydroxyl containing component to help compatibilize the reactive, hydrophilic polymeric IWA of the present invention and the silicone containing components. The hydroxyl containing component that may be used to make the polymers of this invention have at least one polymerizable double bond and at least one hydrophilic functional group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. The hydroxyl containing component may also act as a crosslinking agent. In addition the hydroxyl containing component comprises a hydroxyl group. This hydroxyl group may be a primary, secondary or tertiary alcohol group, and may be located on an alkyl or aryl group. Examples of hydroxyl containing monomers that may be used include but are not limited to 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate and other hydroxyl functional monomers as disclosed in U.S. Pat. Nos. 5,006,622; 5,070,215; 5,256,751 and 5,311,223. Preferred hydroxyl containining monomers include 2-hydroxyethyl methacrylate, and hydroxyl functional monomers including silicone or siloxane functionalities, such as the hydroxyl-functionalized silicone containing monomers disclosed in WO03/022321, and the compatibilizing components comprising at least one active hydrogen and at least one siloxane group as disclosed in WO03/022322, the disclosure of which is incorporated herein by reference. Specific examples of include 2-propenoic acid, 2-methyl-2-hydroxy-3-[3-[1,3,3,3-tetramethyl-1-[trimethylsilyl)oxy]disiloxanyl]propoxy]propyl ester (which can also be named (3-methacryloxy-2-hydroxypropyloxy)propylbis(trimethylsiloxy)methylsilane), 3-methacryloxy-2-hydroxypropyloxy)propyltris(trimethylsiloxy) silane, bis-3-methacryloxy-2-hydroxypropyloxypropyl polydimethylsiloxane, 3-methacryloxy-2-(2-hydroxyethoxy)propyloxy) propylbis(trimethylsiloxy)methylsilane, N-2-methacryloxyethyl-O-(methyl-bis-trimethylsiloxy-3-propyl)silyl carbamate and N,N,N',N'-tetrakis(3-methacryloxy-2-hydroxypropyl)-α,ω-bis-3-aminopropyl-polydimethylsiloxane and mixtures thereof include 2-hydroxyethyl methacrylate, 3-methacryloxy-2-hydroxypropyloxy)propylbis(trimethylsiloxy)methylsilane), 3-methacryloxy-2-hydroxypropyloxy)propyltris(trimethylsiloxy)silane and mixtures thereof are preferred.

When a compatibilizing component is used, effective amounts of compatibilizing component in the polymer formulation include about 5 percent (weight percent, based on the total weight of the reactive components) to about 90 percent, preferably about 10 percent to about 80 percent, most preferably, about 20 percent to about 50 percent.

Alternatively the reactive, hydrophilic polymeric IWAs may be included in hydrophilic hydrogels. Generally these hydrogels are made from the hydrophilic monomers listed above. Commercially available hydrogel formulations include, but are not limited to etafilcon, polymacon, vifilcon, genfilcon A and lenefilcon A.

Generally the reactive components are mixed in a diluent to form a reaction mixture. Suitable diluents are known in the art.

Classes of suitable diluents for silicone hydrogel reaction mixtures include ethers, esters, alkanes, alkyl halides, silanes, amides, alcohols and combinations thereof. Amides and alcohols are preferred diluents with alcohols having 2 to 20 carbons, amides having 10 to 20 carbon atoms derived from primary amines and carboxylic acids having 8 to 20 carbon atoms. In some embodiments primary and tertiary alcohols are preferred. Preferred classes include alcohols having 5 to 20 carbons and carboxylic acids having 10 to 20 carbon atoms.

Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, SiGMA acetate, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol mixtures thereof and the like.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, tert-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like.

Suitable diluents for non-silicone containing reaction mixtures include glycerin, ethylene glycol, ethanol, methanol, ethyl acetate, methylene chloride, polyethylene glycol, polypropylene glycol, low molecular weight PVP, such as disclosed in U.S. Pat. No. 4,018,853, U.S. Pat. No. 4,680,336 and U.S. Pat. No. 5,039,459, including, but not limited to boric acid esters of dihydric alcohols, combinations thereof and the like.

Mixtures of diluents may be used. The diluents may be used in amounts up to about 50% by weight of the total of all components in the reaction mixture. More preferably the diluent is used in amounts less than about 45% and more preferably in amounts between about 15 and about 40% by weight of the total of all components in the reaction mixture.

In another embodiment, the diluent comprises a low molecular weight hydrophilic polymer without photo-polymerizable reactive groups. The diluent may also comprise additional components such as release agents. Suitable release agents are water soluble and aid in lens deblocking.

It is generally necessary to add one or more cross-linking agents, also referred to as cross-linking monomers, to the reaction mixture, such as ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The cross-linking agents are used in the usual amounts, e.g., from about 0.000415 to about 0.0156 mole per 100 grams of reactive components in the reaction mixture. (The reactive components are everything in the reaction mixture except the diluent and any additional processing aids which do not become part of the structure of the polymer.) Alternatively, if the hydrophilic monomers and/or the silicone-containing monomers act as the cross-linking agent, the addition of a crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone-containing monomer which can act as a crosslinking agent and, when present, does not require the addition of a crosslinking monomer to the reaction mixture includes α, ω-bismethacryloxypropyl polydimethylsiloxane.

The reaction mixture may contain additional components such as, but not limited to, UV absorbers, medicinal agents, antimicrobial compounds, reactive tints, pigments, copolymerizable and nonpolymerizable dyes, release agents and combinations thereof.

A polymerization catalyst or initiator is preferably included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ether and a combination of camphorquinone and ethyl 4-(N,N-dimethylamino)benzoate. Commercially available visible light initiator systems include Irgacure 819, Irgacure 1700, Irgacure 1800, frgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DM-BAPO), and the preferred method of polymerization initiation is visible light. The most preferred is bis(2,4,6-trimethylbenzoyl)-phenyl phosphine oxide (Irgacure 819®).

The invention further comprises, consists and consists essentially of a silicone hydrogel containing a covalently attached reactive, hydrophilic, polymeric IWA and biomedical device, ophthalmic device and contact lenses formed from the formulations shown below: (all numbers are preceded by the word "about")

| RHPIWA | OPC | Wt % HM | CC |
|---|---|---|---|
| | | | |
| 1–15 | 5–75, or 5–60, or 10–50 | 0–70, or 5–60, or 10–50 | 0–90, or 10–80, or 20–50 |
| 3–15 | 5–75, or 5–60, or 10–50 | 0–70, or 5–60, or 10–50 | 0–90, or 10–80, or 20–50 |
| 5–12 | 5–75, or 5–60, or 10–50 | 0–70, or 5–60, or 10–50 | 0–90, or 10–80, or 20–50 |

RHPIWA is reactive, hydrophilic polymeric internal wetting agent
OPC is oxygen permeable component
HM is hydrophilic monomer
CC is compatibilizing component The reaction mixtures of the present invention can be formed by any of the methods know to those skilled in the art, such as shaking or stirring, and used to form polymeric articles or devices by known methods.

For example, the biomedical devices of the invention may be prepared by mixing reactive components and the diluent(s) with a polymerization initator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses comprising the polymer of this invention is by the molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product. Then, this polymer/diluent mixture is treated with a solvent to remove the diluent and ultimately replace it with water, producing a silicone hydrogel having a final size and shape which are quite similar to the size and shape of the original molded polymer/diluent article. This method can be used to form contact lenses and is further described in U.S. Pat. Nos. 4,495,313; 4,680,336; 4,889,664; and 5,039,459, incorporated herein by reference.

The biomedical devices, and particularly ophthalmic lenses of the present invention have a balance of properties which makes them particularly useful. Such properties include clarity, water content, oxygen permeability and contact angle. Thus, in one embodiment, the biomedical devices are contact lenses having a water content of greater than about 17%, preferably greater than about 20% and more preferably greater than about 25%.

As used herein clarity means substantially free from visible haze. Preferably clear lenses have a haze value of less than about 150%, more preferably less than about 100%.

Suitable oxygen permeabilities are preferably greater than about 40 barrer and more preferably greater than about 60 barrer.

Also, the biomedical devices, and particularly ophthalmic devices and contact lenses have contact angles (advancing) which are less than about 80°, preferably less than about 70° and more preferably less than about 65°. In some preferred embodiments the articles of the present invention have combinations of the above described oxygen permeability, water content and contact angle. All combinations of the above ranges are deemed to be within the present invention.

The non-limiting examples below further describe this invention.

The dynamic contact angle or DCA, was measured at 23° C., with borate buffered saline, using a Wilhelmy balance. The wetting force between the lens surface and borate buffered saline is measured using a Wilhelmy microbalance while the sample strip cut from the center portion of the lens is being immersed into the saline at a rate of 100 microns/sec. The following equation is used $$F=2\gamma p \cos \theta \text{ or } \theta=\cos^{-1}(F/2\gamma p)$$

where F is the wetting force, γ is the surface tension of the probe liquid, p is the perimeter of the sample at the meniscus and θ is the contact angle. Typically, two contact angles are obtained from a dynamic wetting experiment—advancing contact angle and receding contact angle. Advancing contact angle is obtained from the portion of the wetting experiment where the sample is being immersed into the probe liquid, and these are the values reported herein. At least four lenses of each composition are measured and the average is reported.

The water content was measured as follows: lenses to be tested were allowed to sit in packing solution for 24 hours. Each of three test lens were removed from packing solution using a sponge tipped swab and placed on blotting wipes which have been dampened with packing solution. Both sides of the lens were contacted with the wipe. Using tweezers, the test lens were placed in a weighing pan and weighed. The two more sets of samples were prepared and weighed as above. The pan was weighed three times and the average is the wet weight.

The dry weight was measured by placing the sample pans in a vacuum oven which has been preheated to 60° C. for 30 minutes. Vacuum was applied until at least 0.4 inches Hg is attained. The vacuum valve and pump were turned off and the lenses were dried for four hours. The purge valve was opened and the oven was allowed reach atmospheric pressure. The pans were removed and weighed. The water content was calculated as follows:

Wet weight = combined wet weight of pan and lenses −
weight of weighing pan

Dry weight = combined dry weight of pan and lens −
weight of weighing pan $$\% \text{ water content} = \frac{(\text{wet weight} - \text{dry weight})}{\text{wet weight}} \times 100$$

The average and standard deviation of the water content are calculated for the samples are reported.

Modulus was measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width was loaded into the grips and elongated at a constant rate of strain of 2 in/min. until it broke. The initial gauge length of the sample (Lo) and sample length at break (Lf) were measured. Twelve specimens of each composition were measured and the average is reported. Tensile modulus was measured at the initial linear portion of the stress/strain curve.

Haze is measured by placing a hydrated test lens in borate buffered saline in a clear 20×40×10 mm glass cell at ambient temperature above a flat black background, illuminating from below with a fiber optic lamp (Titan Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

Oxygen permeability (Dk) may be determined by the polarographic method generally described in ISO 9913-1: 1996(E), but with the following variations. The measurement is conducted at an environment containing 2.1% oxygen. This environment is created by equipping the test chamber with nitrogen and air inputs set at the appropriate ratio, for example 1800 ml/min of nitrogen and 200 ml/min of air. The t/Dk is calculated using the adjusted $P_{O2}$. Borate buffered saline was used. The dark current was measured by using a pure humidified nitrogen environment instead of applying MMA lenses. The lenses were not blotted before measuring. Four lenses were stacked instead of using lenses of varied thickness. A curved sensor was used in place of a flat sensor. The resulting Dk value is reported in barrers.

The following abbreviations are used throughout the Examples and have the following meanings.

| | |
|---|---|
| SiGMA | 2-propenoic acid, 2-methyl-2-hydroxy-3-[3-[1,3,3,3-tetramethyl-1-[trimethylsilyl)oxy]disiloxanyl]propoxy] propyl ester |
| DMA | N,N-dimethylacrylamide |
| HEMA | 2-hydroxyethyl methacrylate |
| mPDMS | 800-1000 MW (Mn) monomethacryloxypropyl terminated mono-n-butyl terminated polydimethylsiloxane |
| Norbloc | 2-(2'-hydroxy-5-methacrylyloxyethylphenyl)-2H-benzotriazole |
| CGI 1850 | 1:1 (weight) blend of 1-hydroxycyclohexyl phenyl ketone and bis(2,6-dimethoxybenzoyl)-2,4-4-trimethylpentyl phosphine oxide |
| CGI 819 | 2,4,6-trimethylbenzyldiphenyl phosphine oxide |
| LMWHP | low molecular weight hydrophilic polymer comprised of a poly(N-vinyl pyrrolidone) backbone with either hydroxyl, amine, carboxylic acid, or carboxylate end groups |
| HMWHC | high molecular weight hydrophilic copolymer comprised of poly(N-vinyl pyrrolidone)-co-(9-vinylcarbazole) (97.5/2.5) |
| RHPIWA | reactive, hydrophilic polymeric IWA comprised of a poly(N-vinyl pyrrolidone) backbone with covalently attached photo-polymerizable end groups |
| IPA | isopropyl alcohol |
| D3O | 3,7-dimethyl-3-octanol |
| TEGDMA | tetraethyleneglycol dimethacrylate |
| EGDMA | ethyleneglycol dimethacrylate |
| MMA | methyl methacrylate |
| THF | tetrahydrofuran |
| Dioxane | 1,4-dioxane |

-continued

| | |
|---|---|
| DMF | N,N-dimethylformamide |
| DMAc | N,N-dimethylacetamide |
| PVP low | Poly(N-vinyl pyrrolidone), ~2500 MW |

EXAMPLE 1

9-Vinylcarbazole (0.79 gm, 4.1 mmol) (Aldrich, Milwaukee, Wis.), 2,2'-Azobis[N-(2-carboxyethyl)-2-methylpropionamidine]tetrahydrate (0.16 gm, 0.46 mmol) (Wako Chemicals USA, St. Louis, Mo.) and freshly distilled N-vinyl-2-pyrrolidone (NVP) (15.1 gm, 136 mmol) were added to a 250 mL round bottom flask equipped with magnetic stirrer and nitrogen inlet. Methyl alcohol (19.2 gm) and distilled water (23.4 gm) were added to the reaction mixture. The mixture was degassed using 3 freeze-pump-thaw cycles and then allowed to warm to ambient temperature. The reaction mixture was heated at 60° C. for 16 hours, then precipitated three times using acetone as asolvent to yield a white polymer with Mn, Mw, and polydispersity values of 166,000, 420,000, and 2.6, respectively. Molecular weights were measured by gel permeation chromatography (GPC) using poly(2-vinylpyridine) standards and hexafluoroisopropanol as mobile phase. $^1$H NMR (D$_2$O): δ=7.0-8.2 (bm, 8H, carbazole aromatic H), 3.4-3.8 (bm, 1H, —CH$_2$CH—), 3.3 (bm, 2H, —C[O]NCH$_2$—), 2.0-2.4 (bm, 2H, —C[O]CH$_2$—), 1.8-2.0 (bm, 2H, —CH$_2$CH$_2$CH$_2$—), 1.4-1.7 (bm, 2H, —CH$_2$CH—).

EXAMPLE 2

9-Vinylcarbazole (Aldrich, Milwaukee, Wis.) (1.9 gm, 9.6 mmol), 2,2'-azobis[N-(2-carboxyethyl)-2-methylpropionamidine]tetrahydrate (Wako Chemicals USA, St. Louis, Mo.) (0.56 gm, 1.4 mmol) and freshly distilled N-vinyl-2-pyrrolidone (NVP) (52.8 gm, 475 mmol) were added to a 1 L round bottom flask equipped with magnetic stirrer and nitrogen inlet. Methyl alcohol (231.4 gm) was added to the reaction mixture. The mixture was degassed using 3 freeze-pump-thaw cycles and then allowed to warm to ambient temperature. The reaction mixture was heated at 60° C. for 4 hours, then isolated by precipitation (3 times) into diisopropyl ether to yield a white polymer with Mn, Mw, and polydispersity values of 30,000, 110,000, and 3.7, respectively, using poly(2-vinylpyridine) standards and hexafluoroisopropanol as mobile phase.

EXAMPLE 3

Polymer from Example 2 (27.0 gm, 239 mmol), DMAC (173 gm), 4-dimethylaminopyridine (DMAP, Avocado Research Chemicals, Heysham, England) (1.2 gm, 9.6 mmol), pyridine (20 mL), methacrylic anhydride (Aldrich, Milwaukee, Wis.) (7.43 g, 48.2 mmol) and hydroquinone (50 mg, 0.5 mmol, Aldrich, Milwaukee, Wis.) were charged to a 500 mL round bottom flask equipped with magnetic stirrer and nitrogen inlet. The reaction mixture was heated at 70° C. for 6 hours and then isolated by precipitation into diisopropyl ether (three times) to afford a white solid with Mn, Mw, and polydispersity values of 33,000, 109,000, and 3.3, respectively, using poly(2-vinylpyridine) standards and hexafluoroisopropanol as mobile phase.

EXAMPLE 4

N-vinylpyrrolidone (50.0 gm, 450 mmol), 2-mercaptopropionic acid (Aldrich, Milwaukee, Wis.) (0.97 g, 9.2 mmol), 9-vinylcarbazole (1.8 g, 9.2 mmol), and 2,2'-azobis[N-(2-carboxyethyl)-2-methylpropionamidine]tetrahydrate (Wako Chemicals USA, St. Louis, Mo.) (0.53 gm, 1.3 mmol), DMAC (143 gm), and distilled water (40 mL) were charged to a 500 mL round bottom flask equipped with a nitrogen inlet and magnetic stirrer. The reaction mixture was frozen using an external CO$_2$/acetone bath and then placed under vacuum. The solution was backfilled with nitrogen, thawed, and frozen again under vacuum for a total of 3 freeze-pump-thaw cycles. The solution was heated to 60° C. under nitrogen for 6 hours. Hydroquinone (50 mg, 0.5 mmol, Aldrich, Milwaukee, Wis.) was added to the reaction mixture, which was then cooled to 5° C. 1-Hydroxybenzotriazole (Aldrich, Milwaukee, Wis.) (3.7 gm, 28 mmol), 2-aminoethyl methacrylate hydrochloride (Aldrich, Milwaukee, Wis.) (4.6 gm, 28 mmol), and 1-[3-(dimethylamino)propyl]-3-ethylcarbodiimide hydrochloride (EDC) (Aldrich, Milwaukee, Wis.) (5.3 gm, 28 mmol) were added and the mixture was stirred for 1 hour at 5° C., followed by an additional 20 hours at room temperature. The reaction mixture was diluted with DMAC (250 mL) and then poured slowly into 70:30 t-butyl methyl ether/hexanes to precipitate out the white solid (90 percent). The polymer was dissolved in 2-propanol and re-precipitated an additional 2 times. The resultant PVP macromer had Mn, Mw, and polydispersity values of 41,000, 155,000, and 3.7, respectively.

EXAMPLE 5

N-vinylpyrrolidone (42.6 gm, 384 mmol), 9-vinylcarbazole (0.59 gm, 3.0 mmol), 2,2'-azobis{2-[1-(2-hydroxyethyl)-2-imidazolin-2-yl]propane}dihydrochloride (Wako Chemicals USA, St. Louis, Mo.) (2.67 gm, 7.89 mmol), and methyl alcohol (160 gm) were charged to a 500 mL round bottom flask equipped with a nitrogen inlet and magnetic stirrer. The reaction mixture was subjected to 3 freeze-pump-thaw cycles and then heated to 60° C. under nitrogen for 6 hours. The polymer was isolated as a white solid (85 percent) by precipitation into diisopropyl ether 3 times and then dried.

The resultant polymer (15.8 gm, 141 mmol) was dissolved in anhydrous 1,4-dioxane (Aldrich, Milwaukee, Wis.) (400 mL). Hydroquinone (50 mg, 0.5 mmol) was added to the reaction mixture, followed by 2-isocyanatoethyl methacrylate (Aldrich, Milwaukee, Wis.) (2.2 gm, 14 mmol) and 100 microL of 0.33M stannous octoate (made by dissolving stannous octoate (Aldrich, Milwaukee, Wis.) in anhydrous toluene). The reaction mixture was heated to 70° C. for 8 hours and then poured slowly into diisopropyl ether to yield a white solid (88 percent). The polymer was re-dissolved in 2-propanol and precipitated 2 additional times. The resultant PVP macromer had Mn, Mw, and polydispersity values of 8,000, 46,000, and 6.0, respectively.

EXAMPLE 6

N-vinylpyrrolidone (50.4 gm, 453 mmol), 2-mercaptopropionic acid (Aldrich, Milwaukee, Wis.) (1.0 gm, 9.2 mmol), 9-vinylcarbazole (1.78 gm, 9.4 mmol), and 2,2'-azobis(2-methylpropionamide)dihydrochloride (Wako Chemicals USA, St. Louis, Mo.) (2.5 gm, 9.3 mmol), DMAC (150 gm), and distilled water (100 mL) were charged to a 500 mL round bottom flask equipped with a nitrogen inlet and magnetic stirrer. The reaction mixture was frozen using an external $CO_2$/acetone bath and then placed under vacuum. The solution was backfilled with nitrogen, thawed, and frozen again under vacuum for a total of 3 freeze-pump-thaw cycles. The solution was heated to 60° C. under nitrogen for 6 hours. Hydroquinone (50 mg, 0.5 mmol) was added to the reaction mixture, which was then cooled to 10° C. 1-Hydroxybenzotriazole (3.9 gm, 30 mmol), 2-aminoethyl methacrylate hydrochloride (4.6 gm, 28 mmol), and EDC (5.7 gm, 30 mmol) were added and the mixture was stirred for 1 hour at 5° C., followed by an additional 40 hours at room temperature. The reaction mixture was diluted with DMAC (200 mL) and then poured slowly into 70:30 t-butyl methyl ether/hexanes to precipitate out the white solid (84 percent).

The polymer was dissolved in 2-propanol and re-precipitated an additional 2 times.

The resultant PVP macromer had Mn, Mw, and polydispersity values of 9,800, 44,000, and 4.5, respectively.

EXAMPLE 7

Contact Lens Formation

The reaction components and diluent (tert-amyl alcohol) listed in Table 2 were mixed together with stirring, shaking, or rolling for at least about 3 hours at 23° C., until all components were dissolved. The reactive components are reported as weight percent of all reactive components and the diluent and low molecular weight PVP (PVP low) are weight percents of reaction mixture.

The reactive components were purged for approximately 15 minutes using $N_2$. Approximately 40-50 microliters of the reaction formulations were pipetted onto clean polypropylene concave mold halves and covered with the complementary polypropylene convex mold halves. The mold halves were compressed and the mixtures were cured at 55° C. for about 30 minutes in the presence of visible light (0.4 mW/cm² using Philips TL 20W/03T fluorescent bulbs, as measured by an International Light radiometer/photometer). The molds were allowed to cool to room temperature. The top mold halves were removed and the lenses gently removed using tweezers. The lenses were released in water at 90° C. for about 20 minutes and then placed in vials containing borate buffered packing solution.

TABLE 2

| Component | Example | | | | | |
|---|---|---|---|---|---|---|
| | 7A | 7B | 7C | 7D | 7E | 7F |
| SiGMA | 30.5 | 30.5 | 30.5 | 30.5 | 30 | 30 |
| Ex 1 | 6.1 | 0 | 0 | 0 | 0 | 0 |

TABLE 2-continued

| Component | Example | | | | | |
|---|---|---|---|---|---|---|
| | 7A | 7B | 7C | 7D | 7E | 7F |
| Ex 2 | 0 | 6.1 | 0 | 0 | 0 | 0 |
| Ex 3 | 0 | 0 | 6.1 | 0 | 0 | 0 |
| Ex 4 | 0 | 0 | 0 | 6.1 | 0 | 0 |
| Ex 5 | 0 | 0 | 0 | 0 | 6 | 0 |
| Ex 6 | 0 | 0 | 0 | 0 | 0 | 6 |
| DMA | 31.5 | 31.5 | 31.5 | 31.5 | 31 | 31 |
| mPDMS | 22.3 | 22.3 | 22.3 | 22.3 | 22 | 22 |
| HEMA | 8.6 | 8.6 | 8.6 | 8.6 | 8.5 | 8.5 |
| Norbloc | 0 | 0 | 0 | 0 | 1.5 | 1.5 |
| CGI 1850 | 0 | 0 | 0 | 0 | 0 | 0 |
| CGI 819 | 0.23 | 0.23 | 0.23 | 0.23 | 0.23 | 0.23 |
| TEGDMA | 0 | 0 | 0 | 0 | 0 | 0 |
| EGDMA | 0.76 | 0.76 | 0.76 | 0.76 | 0.75 | 0.75 |
| PVP low | 11 | 11 | 11 | 11 | 11 | 11 |
| t-amyl alcohol percent | 29 | 29 | 29 | 29 | 29 | 29 |

The reactive, hydrophilic polymeric IWAs (RHPIWA) were synthesized in the presence of small amounts (~1 mol percent) of fluorescent vinyl monomers. Covalently attached fluorescent "probes", or fluorophores, were used to detect the diffusion of unreacted monomers from the production of the reactive, hydrophilic polymeric IWAs from the contact lenses. The concentration of fluorescent probe in the RHPIWA is low enough so that the physical properties of the labeled RHPIWA are similar to that of unlabeled RHPIWA.

The fluorescent probes and fluorescently labeled macromers were first tested to determine whether conditions necessary to make lenses, such as for example, light intensity and heat, affect the emission of fluorescence of the fluorophore. The resultant fluorescently labeled macromers were then combined with reactive components and diluents to make contact lenses. The release of PVP macromers labeled with fluorescent carbazole groups was measured from the extraction media using a Shimadzu RF5301-PC spectrofluorometer (excitation $\lambda$=343 nm, emission $\lambda$=348 nm, slit width=3 nm). A standard calibration curve of PVP macromer standards was used to correlate the amount of PVP macromer release from lenses. As a control, a high molecular weight hydrophilic copolymer (HMWHC) was used based on PVP (containing 2.5 mol percent carbazole groups) with Mn, Mw, and PD values of 94,800, 511,000, and 5.4, respectively. The molecular weight of the internal wetting agent ($M_n$), and amount of internal wetting agent extracted after 50-100 hrs are shown in Table 3.

TABLE 3

| | Ex. # | | | | | |
|---|---|---|---|---|---|---|
| | 7A | 7B | 7C | 7D | 7E | 7F |
| $M_n$ | 166,000 | 30,000 | 33,000 | 41,000 | 8,000 | 9,800 |
| Extraction Time (hrs) | 100 | 104 | 96 | 52 | 102 | 99 |
| Internal wetting agent | 420 | 110 | 109 | 155 | 46 | 44 |
| $M_w \times 10^{-3}$ (PDI) | (2.6) | (3.7) | (3.3) | (3.7) | (6.0) | (4.5) |
| Percent wetting agent released | 12 | 50 | 35 | 5 | 25 | 20 |

The results of Examples 7A through 7F show that the reaction mixture components and their amounts may be varied. All lenses showed low haze.

The reactive, hydrophilic polymeric internal wetting agents in Examples 7C through 7F) were comparable or lower in molecular weight than the low molecular weight hydrophilic polymer of Example 2 (used in formulation 7B) having no photo-polymerizable groups. The percent release of the reactive, hydrophilic polymeric IWAs (Examples 7C-F) from contact lenses was lower (5-35%) as compared to polymers without photo-polymerizable groups (Example 7B, 50%). Example 7A used a non-reactive high molecular weight hydrophilic copolymers. FIG. 1 shows the percent of internal wetting agent loss in IPA as a function of time. Example 7D, which comprises a reactive, hydrophilic polymeric IWA lost less than about 5% of the IWA, while Example 7A (which contained a non-reactive hydrophilic, polymeric IWA) lost about 12% of the IWA. Based on Example 4, comparable and even slower release rates can be achieved using lower molecular hydrophilic polymeric IWAs with photo-polymerizable end group(s).

The Examples also show that reactive, hydrophilic polymeric IWAs may be synthesized using several synthetic routes, and resulting in resulting in reactive, hydrophilic polymeric IWAs with different structures, particularly at the end groups.

The lenses from Example 7F were analyzed to determine contact angle, water content and mechanical properties. The results are shown in Table 4, below.

TABLE 4

| | |
|---|---|
| Advancing contact angle | 52° |
| Water content | 45.2% |
| Modulus | 110 psi |
| Elongation at break | 124% |

Thus the reactive, hydrophilic polymeric IWAs produce contact lenses with desirable properties.

EXAMPLE 8

Reactive, hydrophilic polymeric IWA was synthesized as in Example 3, except without the use of 9-vinylcarbazole to yield a white polymer with Mn, Mw, and polydispersity values of 38,000, 113,000, and 3.0, respectively.

EXAMPLE 9

Reactive, hydrophilic polymeric IWA was synthesized as in Example 4, except without the use of 9-vinylcarbazole to yield a white polymer with Mn, Mw, and polydispersity values of 34,500, 138,000, and 4.0, respectively.

EXAMPLE 10

Reactive, hydrophilic polymeric IWA was synthesized as in Example 5, except without the use of 9-vinylcarbazole to yield a white polymer with Mn, Mw, and polydispersity values of 8,500, 42,000, and 4.9, respectively.

EXAMPLE 11

Reactive, hydrophilic polymeric IWA was synthesized as in Example 6, except without the use of 9-vinylcarbazole to yield a white polymer with Mn, Mw, and polydispersity values of 10,000, 40,000, and 4.0, respectively.

EXAMPLE 12

Contact Lens Formation

Lenses containing the reactive, hydrophilic polymeric internal wetting agents of Examples 8-11 (no fluorophore) were made as in Example 7. The cure intensity, temperature, and time were maintained 4.0 mW/cm$^2$, 55° C., and 12 minutes, respectively. Again, low haze was observed in all lenses.

EXAMPLE 13

NVP (50.5 gm, 454 mmol), vinyl acetate (6.7 gm, 78 mmol), 9-Vinylcarbazole (1.0 gm, 5.4 mmol), 2,2'-Azobis [N-(2-carboxyethyl)-2-methylpropionamidine]tetrahydrate (0.578 gm, 1.39 mmol), methyl alcohol (170 gm), and distilled water (27 gm) were added to a 500 mL round bottom flask equipped with magnetic stirrer and nitrogen inlet. The mixture was degassed using 3 freeze-pump-thaw cycles and then allowed to warm to ambient temperature. The reaction mixture was heated at 60° C. for 6 hours, and then isolated by precipitation (3 times) into diisopropyl ether to yield a white polymer. The polymer was redissolved in distilled water (1 L) and NaOH was added (3.6 gm, 89 mmol). The reaction mixture was heated to 70° C. for 4 hours and then concentrated by rotary evaporation of the solvent. The polymer was precipitated from cold acetone, redissolved in 2 L distilled water, and dialyzed for 72 hours against water and 48 hours against isopropyl alcohol using 3500 molecular weight cut-off Spectra/Por® dialysis membrane (purchased from VWR). The polymer was isolated by removal of solvent to yield an off-white solid with Mn, Mw, and polydispersity values of 49,000, 191,000, and 3.9, respectively.

EXAMPLE 14

The high molecular weight polymer product from Example 13 (21 gm, 200 mmol), anhydrous triethylamine (11.6 gm, 115 mmol), 4-(dimethylamino)pyridine (Aldrich, Milwaukee, Wis.) (6.1 gm, 50 mmol), hydroquinone (Aldrich, Milwaukee, Wis.) (50 mg, 0.5 mmol) and anhydrous 1,4-dioxane (300 mL) were charged to a 500 mL round bottom flask equipped with a nitrogen inlet and magnetic stirrer. Methacryloyl chloride (Aldrich, Milwaukee, Wis.) (6.0 gm, 57 mmol) was added dropwise to the reaction mixture. The mixture was subsequently heated at 60° C. for 4 hours. The polymer was isolated by precipitation into 50/50 t-butyl methyl ether/hexanes to yield an off-white solid with Mn, Mw, and polydispersity values of 54,000, 200,000, and 3.7, respectively.

EXAMPLE 15

NVP (50.7 gm, 457 mmol), vinyl acetate (3.7 gm, 43 mmol), 9-vinylcarbazole (0.90 gm, 4.9 mmol), 2,2'-Azobis [N-(2-carboxyethyl)-2-methylpropionamidine]tetrahydrate (0.38 gm, 0.91 mmol), methyl alcohol (75 gm), and distilled water (75 gm) were added to a 500 mL round bottom flask equipped with magnetic stirrer and nitrogen inlet. The mixture was degassed using 3 freeze-pump-thaw cycles and then allowed to warm to ambient temperature. The reaction mixture was heated at 60° C. for 18 hours, and then isolated by precipitation (3 times) into 50/50 diisopropyl ether/ hexanes to yield a white polymer. The polymer was redissolved in distilled water (1 L) and NaOH was added (1.7 gm, 43 mmol). The reaction mixture was heated to 60° C. for 6 hours and then concentrated by rotary evaporation of the solvent at 60° C. The polymer was precipitated from 70/30 acetone/hexanes, redissolved in 2 L distilled water, and dialyzed for 72 hours against water and 48 hours against isopropyl alcohol using 3500 molecular weight cut-off Spectra/Por® dialysis membrane (purchased from VWR). The polymer was isolated by removal of solvent to yield an off-white solid with Mn, Mw, and polydispersity values of 86,000, 310,000, and 3.6, respectively.

EXAMPLE 16

The high molecular weight polymer product from Example 15 (25 gm, 240 mmol), hydroquinone (Aldrich, Milwaukee, Wis.) (50 mg, 0.5 mmol), 2-isocyanatoethyl methacrylate (Aldrich, Milwaukee, Wis.) (3.21 gm, 20.4 mmol) and 100 milliliters of 0.33M stannous octoate [made by dissolving stannous octoate (Aldrich, Milwaukee, Wis.) in anhydrous toluene], and anhydrous 1,4-dioxane (300 mL) were charged to a 500 mL round bottom flask equipped with a nitrogen inlet and magnetic stirrer. The reaction mixture was heated to 70° C. for 8 hours and then poured slowly into diisopropyl ether to yield a white solid (92 percent). The polymer was dissolved in 2-propanol and precipitated 2 additional times affording an off-white solid with Mn, Mw, and polydispersity values of 86,000, 320,000, and 3.7, respectively.

EXAMPLE 17

The reaction components and diluent (tert-amyl alcohol) listed in Table 3 were mixed together and processed to make lenses in accordance with the procedure described in Example 7, above.

In one embodiment, reactive, hydrophilic polymeric IWAs were synthesized in the presence of small amounts (~1 mol percent) of fluorescent vinyl monomers. The general structure is shown in Formulae XIX, where 9-vinylcarbazole units are present between 0.1 and 2 mol percent.

VI

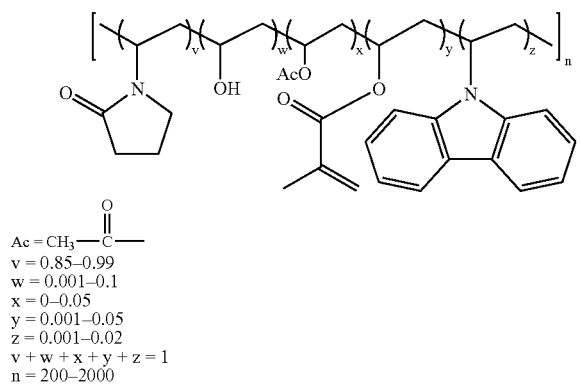

$Ac = CH_3-\overset{O}{\underset{\|}{C}}-$
$v = 0.85–0.99$
$w = 0.001–0.1$
$x = 0–0.05$
$y = 0.001–0.05$
$z = 0.001–0.02$
$v + w + x + y + z = 1$
$n = 200–2000$ Small amounts of covalently attached fluorescent "probes", or fluorophores, were used to detect the diffusion of the polymers listed in Table 3 from contact lenses, as described in Example 7. The lens compositions, molecular weight of the internal wetting agent, and amount of internal wetting agent extracted after 50-100 hrs are shown in Table 5, below.

TABLE 5

| Component | 17A | 17B | 17C | 17D | 17E | 17F |
|---|---|---|---|---|---|---|
| SiGMA | 30.5 | 30.5 | 30.5 | 30.5 | 30 | 30 |
| Ex 1 | 6.1 | 0 | 0 | 0 | 0 | 0 |
| Ex 2 | 0 | 6.1 | 0 | 0 | 0 | 0 |
| Ex 13 | 0 | 0 | 6.1 | 0 | 0 | 0 |
| Ex 14 | 0 | 0 | 0 | 6.1 | 0 | 0 |
| Ex 15 | 0 | 0 | 0 | 0 | 6.1 | 0 |
| Ex 16 | 0 | 0 | 0 | 0 | 0 | 6.1 |
| DMA | 31.5 | 31.5 | 31.5 | 31.5 | 31.5 | 31.5 |
| MPDMS | 22.3 | 22.3 | 22.3 | 22.3 | 22.3 | 22.3 |
| HEMA | 8.6 | 8.6 | 8.6 | 8.6 | 8.6 | 8.6 |
| Norbloc | 0 | 0 | 0 | 0 | 0 | 0 |
| CGI 819 | 0.23 | 0.23 | 0.23 | 0.23 | 0.23 | 0.23 |
| TEGDMA | 0 | 0 | 0 | 0 | 0 | 0 |
| EGDMA | 0.76 | 0.76 | 0.76 | 0.76 | 0.76 | 0.76 |
| PVP low | 11 | 11 | 11 | 11 | 11 | 11 |
| t-amyl alcohol % | 29 | 29 | 29 | 29 | 29 | 29 |
| Percent PVP macromer released from lens after extraction in 2-propanol | | | | | | |
| Extraction Time (hrs) | 100 | 104 | 98 | 96 | 100 | 99 |
| IWA $M_w \times 10^{-3}$ (PDI) | 420 (2.6) | 110 (3.7) | 191 (3.9) | 200 (3.7) | 310 (3.6) | 320 (3.7) |
| Weight % release of IWA | 12 | 50 | 26 | 0.3 | 18 | 0.4 |

The results of Examples 17A through F show that the reaction mixture components and their amounts may be varied. All lenses showed low haze.

As shown in Table 5, the rate of release of the polymers without reactive groups (Examples 17C and 17E) was faster than that of the high molecular weight control (Example 17A) and slower than that of the low molecular weight control (Example 17B) after ~100 hours in isopropanol. Examples 17D and 17F, which contained reactive, hydrophilic polymeric IWAs of the present invention, displayed insignificant release of the internal wetting agents. This is significant since preservation of the internal wetting agent helps maintain lens wettability in addition to other previously described lens properties since the initial weight percent of components in the reaction mixture remains relatively constant after curing and extraction in organic solvents.

EXAMPLE 18

Synthesis was carried out as in Example 13 without the use of 9-vinylcarbazole. In addition, methyl alcohol in the reaction mixture was replaced by an equal weight of distilled water. Polymer Mn, Mw, and polydispersity was: 45,000, 225,000, and 5.0.

EXAMPLE 19

Synthesis was carried out as in Example 14 without the use of 9-vinylcarbazole. In addition, methyl alcohol in the reaction mixture was replaced by an equal weight of distilled water. Polymer Mn, Mw, and polydispersity were: 49,000, 230,000, and 4.7.

EXAMPLE 20

Lenses containing the low molecular weight hydrophilic polymer of Example 18 and the reactive, hydrophilic polymer IWA of Example 19 were made as in Example 17 using

What is claimed is:

1. A silicone hydrogel formed from a reaction mixture comprising at least one oxygen permeable component and at least one reactive, hydrophilic polymeric internal wetting agent derived from at least one polymer selected from the group consisting of polymers of Formulae of II, IV, VI and VII

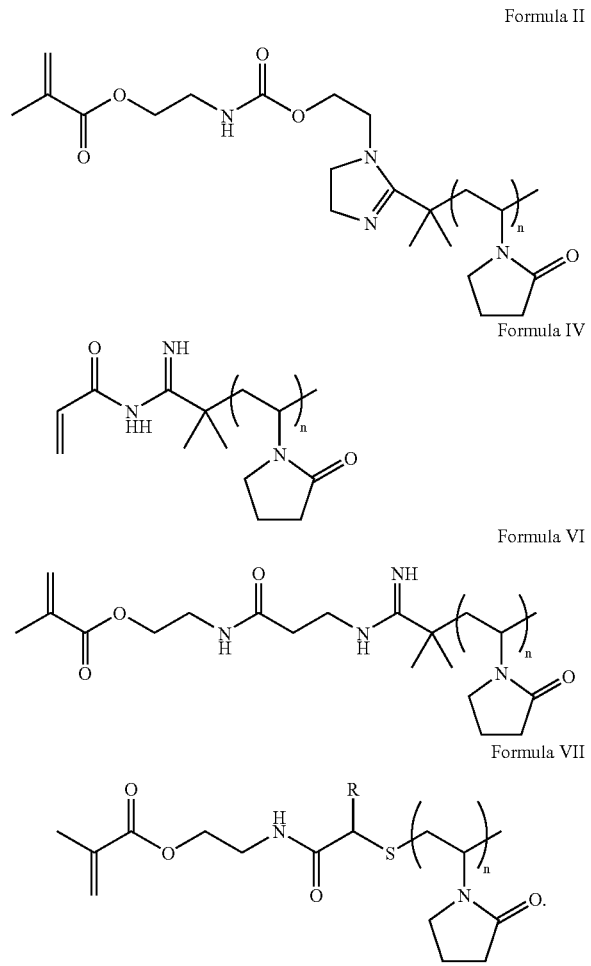

Formula II

Formula IV

Formula VI

Formula VII

2. The hydrogel of claim 1 wherein said internal wetting agent has a Mw of about 5,000 to about 2,000,000 Daltons.

3. The hydrogel of claim 1 wherein said internal wetting agent has a Mw of about 5,000 to about 180,000 Daltons.

4. The hydrogel of claim 1 wherein said internal wetting agent has a Mw of about 5,000 to about 150,000 Daltons.

5. The hydrogel of claim 1 wherein said internal wetting agent has a Mw of about 60,000 to about 2,000,000 Daltons.

6. The hydrogel of claim 1 wherein said internal wetting agent has a Mw of about 180,000 to about 1,500,000 Daltons.

7. The hydrogel of claim 1 comprising a mixture of reactive, hydrophilic polymeric internal wetting agents.

8. The hydrogel of claim 1 wherein said internal wetting agent is derived from at least one polymer selected from the group consisting of polyamides, polylactones, polyimides, polylactams and functionalized polyamides, polylactones, polyimides, polylactams and copolymers and mixtures thereof.

9. The hydrogel of claim 1 wherein said reactive, hydrophilic polymeric internal wetting agent is present in an amounts from about 1 to about 15 weight percent, based upon total weight of all reactive components.

10. The hydrogel of claim 1 wherein said internal wetting agent is present in an amounts from about 3 to about 15 percent, based upon total weight of all reactive components.

11. The hydrogel of claim 1 wherein said internal wetting agent is present in an amounts from about 5 to about 12 percent, based upon total weight of all reactive components.

12. The hydrogel of claim 1 wherein said oxygen permeable component comprises at least one silicone containing component.

13. The hydrogel of claim 12 wherein said at least one silicone containing component is selected from the group consisting of silicone containing monomers, silicone containing macromers and mixtures thereof.

14. The hydrogel of claim 12 wherein said at least one silicone containing component is selected from the group consisting of polysiloxyalkyl(meth)acrylic monomers, poly(organosiloxane) prepolymers, silicone containing vinyl carbonate monomers, silicone containing vinyl carbamate monomers, and mixtures thereof.

15. The hydrogel of claim 1 further comprising at least one hydrophilic monomer.

16. The hydrogel of claim 15 wherein said hydrophilic monomer is present in amounts up to about 60 weight % based upon weight of all reactive components.

17. The hydrogel of claim 15 wherein said hydrophilic monomer is present in amounts between about 10 to about 60 weight % based upon weight of all reactive components.

18. The hydrogel of claim 15 wherein said hydrophilic monomer is present in amounts between about 20 to about 40 weight % based upon weight of all reactive components.

19. The hydrogel of claim 15 wherein said hydrophilic monomer is selected from the group consisting of N,N-dimethyl acrylamide (DMA), 2-hydroxyethyl acrylate, 2-hydroxyethyl methacrylate, glycerol methacrylate, 2-hydroxyethyl methacrylamide, N-vinylpyrrolidone, polyethyleneglycol monomethacrylate, and mixtures thereof.

20. The hydrogel of claim 1 further comprising at least one compatibilizing component.

21. The hydrogel of claim 20 wherein said compatibilizing component is selected from hydroxyl containing monomers and macromers.

22. The hydrogel of claim 20 wherein said compatibilizing component is selected from the group consisting of 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate and hydroxyl functional monomers comprising silicone or siloxane groups and mixtures thereof.

23. The hydrogel of claim 20 wherein said compatibilizing component is selected from the group consisting of 2-hydroxyethyl methacrylate, 3-methacryloxy-2-hydroxypropyloxy)propylbis(trimethylsiloxy)methylsilane, 3-methacryloxy-2-hydroxypropyloxy)propyltris(trimethylsiloxy)silane, bis-3-methacryloxy-2-hydroxypropyloxypropyl polydimethylsiloxane, 3-methacryloxy-2-(2-hydroxyethoxy)propyloxy) propylbis(trimethylsiloxy)methylsilane, N-2-methacryloxyethyl-O-(methyl-bis-trimethylsiloxy-3- propyl)silyl carbamate and N,N,N',N'-tetrakis(3-methacryloxy-2-hydroxypropyl)-α,ω-bis-3-aminopropyl-polydimethylsiloxane and mixtures thereof.

24. The hydrogel of claim 20 wherein said compatibilizing component is selected from the group consisting of 2-hydroxyethyl methacrylate, 3-methacryloxy-2-hydroxypropyloxy)propylbis(trimethylsiloxy)methylsilane), 3-methacryloxy-2-hydroxypropyloxy)propyltris(trimethylsiloxy)silane and mixtures thereof.

25. The hydrogel of claim 20 wherein said compatibilizing component is present in amounts between about 5 to about 90 weight percent, based on total weight of the reactive components.

26. The hydrogel of claim 20 wherein said compatibilizing component is present in amounts between about 10 to about 80 weight percent based on total weight of the reactive components.

27. The hydrogel of claim 20 wherein said compatibilizing component is present in amounts between about 20 to about 50 weight percent, based on total weight of the reactive components.

28. A contact lens formed from the hydrogel of claim 1.

29. A silicone hydrogel formed from a reaction mixture comprising at least one oxygen permeable component and at least one reactive, hydrophilic polymeric internal wetting agent wherein said reactive, hydrophilic polymeric internal wetting agent comprises a reactive high molecular weight copolymer derived from monomers comprising vinyllactam monomers and vinyl carboxylate monomers.

30. The hydrogel of claim 29 wherein said reactive, hydrophilic polymeric internal wetting agent has a molecular weight (weight average) of at least about 60,000 Daltons.

31. The hydrogel of claim 29 wherein said reactive, hydrophilic polymeric internal wetting agent has a molecular weight (weight average) of between about 60,000 to about 750,000 Daltons.

32. The hydrogel of claim 29 wherein said reactive, hydrophilic polymeric internal wetting agent has a molecular weights (weight average) of between about 180,000 to about 500,000 Daltons.

33. The hydrogel of claim 29 wherein said vinyllactams monomers are selected from the group consisting of N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl4,6-dimethyl-2-caprolactam, N-vinyl-3,5,7-trimethyl-2-caprolactam, N-vinylmaleimide, vinylsuccinimide and mixtures thereof.

34. The hydrogel of claim 29 wherein said vinyllactam monomers are selected from the group consisting of heterocyclic monomers containing 4 carbon atoms in the heterocyclic ring.

35. The hydrogel of claim 29 wherein said vinyllactams monomer comprises N-vinyl-2-pyrrolidone.

36. The hydrogel of claim 29 wherein said vinyl carboxylate monomers are selected from the group consisting of compounds having 1 to 10 carbon atoms and both vinyl and carboxylate functionality.

37. The hydrogel of claim 29 wherein said vinyl carboxylate monomers are selected from the group consisting of vinyl heptanoate, vinyl hexanoate, vinyl pentanoate, vinyl butanoate, vinyl propanoate (vinyl propionate), vinyl ethanoate (vinyl acetate) and mixtures thereof.

38. The hydrogel of claim 29 wherein said vinyl carboxylate monomer comprises vinyl acetate.

39. The hydrogel of claim 29 wherein said reactive, hydrophilic polymeric internal wetting agent is selected from the group consisting of compounds of Formula IX, X

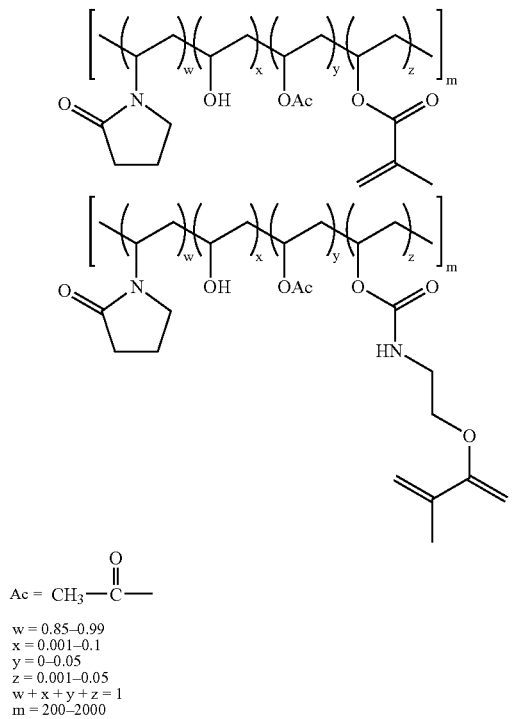

$Ac = CH_3-\overset{O}{\underset{\|}{C}}-$ w = 0.85–0.99
x = 0.001–0.1
y = 0–0.05
z = 0.001–0.05
w + x + y + z = 1
m = 200–2000 and mixtures thereof.

* * * * *